US00PP37725P3

(12) United States Plant Patent
Forgotson et al.

(10) Patent No.: US PP37,725 P3
(45) Date of Patent: Oct. 6, 2026

(54) ***SHEPHERDIA* PLANT NAMED 'Torrey'**

(50) Latin Name: ***Shepherdia argentea* x *Sheperdia rotundifolia***
Varietal Denomination: Torrey

(71) Applicants: Chalita Forgotson, Logan, UT (US); Heidi Kratsch, Logan, UT (US)

(72) Inventors: Chalita Forgotson, Logan, UT (US); Heidi Kratsch, Logan, UT (US)

(73) Assignee: Utah State University, Logan, UT (US)

( * ) Notice: Subject to any disclaimer, the term of this patent is extended or adjusted under 35 U.S.C. 154(b) by 21 days.

(21) Appl. No.: 19/320,567

(22) Filed: Sep. 5, 2025

(65) Prior Publication Data

US 2026/0076278 P1 Mar. 12, 2026

Related U.S. Application Data

(60) Provisional application No. 63/691,736, filed on Sep. 6, 2024.

(51) Int. Cl.

| | |
|---|---|
| ***A01H 5/00*** | (2018.01) |
| ***A01H 5/12*** | (2018.01) |
| ***A01H 6/00*** | (2018.01) |

(52) U.S. Cl.
USPC ..... Plt./226
CPC ..... *A01H 6/00* (2018.05); *A01H 5/12* (2013.01)

(58) Field of Classification Search
USPC ..... Plt./226
See application file for complete search history.

(56) References Cited

PUBLICATIONS

Chen et al. "Nodulation and Plant Growth of *Shepherdia x utahensis* 'Torrey' Topdressed with Controlled-release Fertilizer," HortScience 55 (12):1956-1962, 2020.*
Chen et al. "Nodulation of *Shepherdia x utahensis* 'Torrey' and the Diversity of Symbiotic Frankia Strains," HortScience 56 (7):762-768, 2021.*

* cited by examiner

*Primary Examiner* — Susan McCormick Ewoldt
(74) *Attorney, Agent, or Firm* — Weatherly IP Solutions, LLC; James M. Weatherly; Karen P. Bechtold

(57) ABSTRACT

A new *Shepherdia* plant particularly distinguished by having a USDA plant hardiness zone hardier than its pollen parent, *Shepherdia rotundifolia*; outstanding silvery blue foliage which closely resembles the foliage of its pollen parent the Round Leaf Buffaloberry *Shepherdia rotundifolia*; and ease of propagation and ability to be grown well in a cultivated setting with drought and cold tolerant tolerance, is disclosed.

2 Drawing Sheets

Genus and species: *Sheperdia argentea* x *Sheperdia rotundifolia.*
Variety denomination: 'Torrey'.

BACKGROUND OF THE NEW PLANT

The present invention comprises a new and distinct variety of Utah Buffaloberry, botanically known as *Sheperdia argentea* x *Sheperdia rotundifolia*, and hereinafter referred to by the variety name 'Torrey'. 'Torrey' originated from a cross between an unnamed female *Shepherdia argentea* plant and an unnamed male *Shepherdia rotundifolia* plant.

In April 2008, a cross was made between an unnamed female *Shepherdia argentea* plant and an unnamed male *Shepherdia rotundifolia* plant and seed was collected in Logan, Utah. A plant was selected in Fall of 2010 and named and subsequently named 'Torrey'. In the fall of 2010, 'Torrey' was first vegetatively propagated by cuttings in Logan, Utah, and was found to reproduce true to type in successive generations of asexual propagation via shoot cuttings.

SUMMARY

The following are the most outstanding and distinguishing characteristics of this new variety when grown under normal horticultural practices in Logan, Utah.

1. One USDA plant hardiness zone hardier than its pollen parent, *Shepherdia rotundifolia.*
2. Outstanding silvery blue foliage which closely resembles the foliage of its pollen parent the Round Leaf Buffaloberry *Shepherdia rotundifolia.*
3. Ease of propagation and ability to be grown well in a cultivated setting.
4. Drought and cold tolerance.

DESCRIPTION OF THE PHOTOGRAPHS

Figure 1:
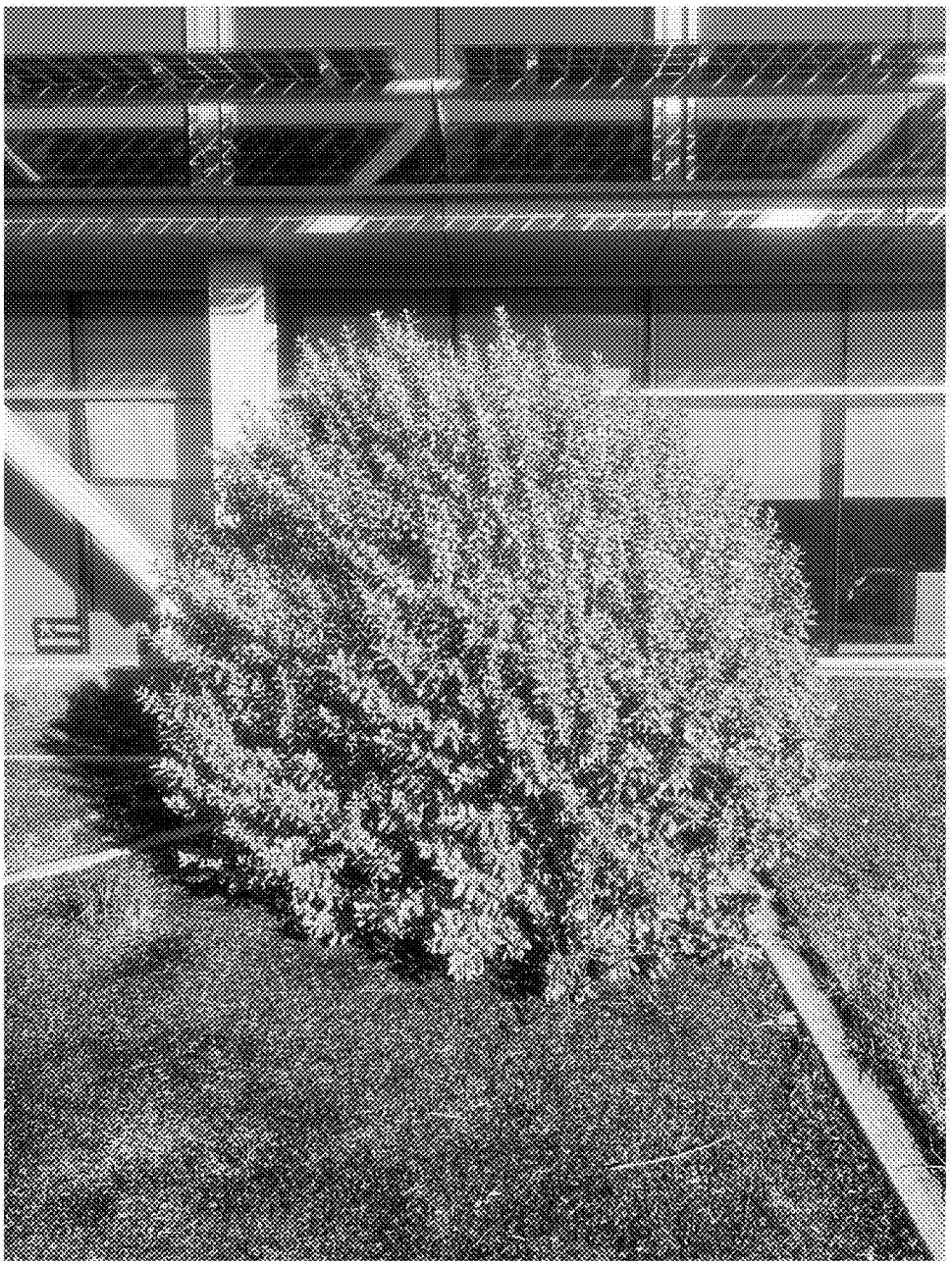
Figure 2:
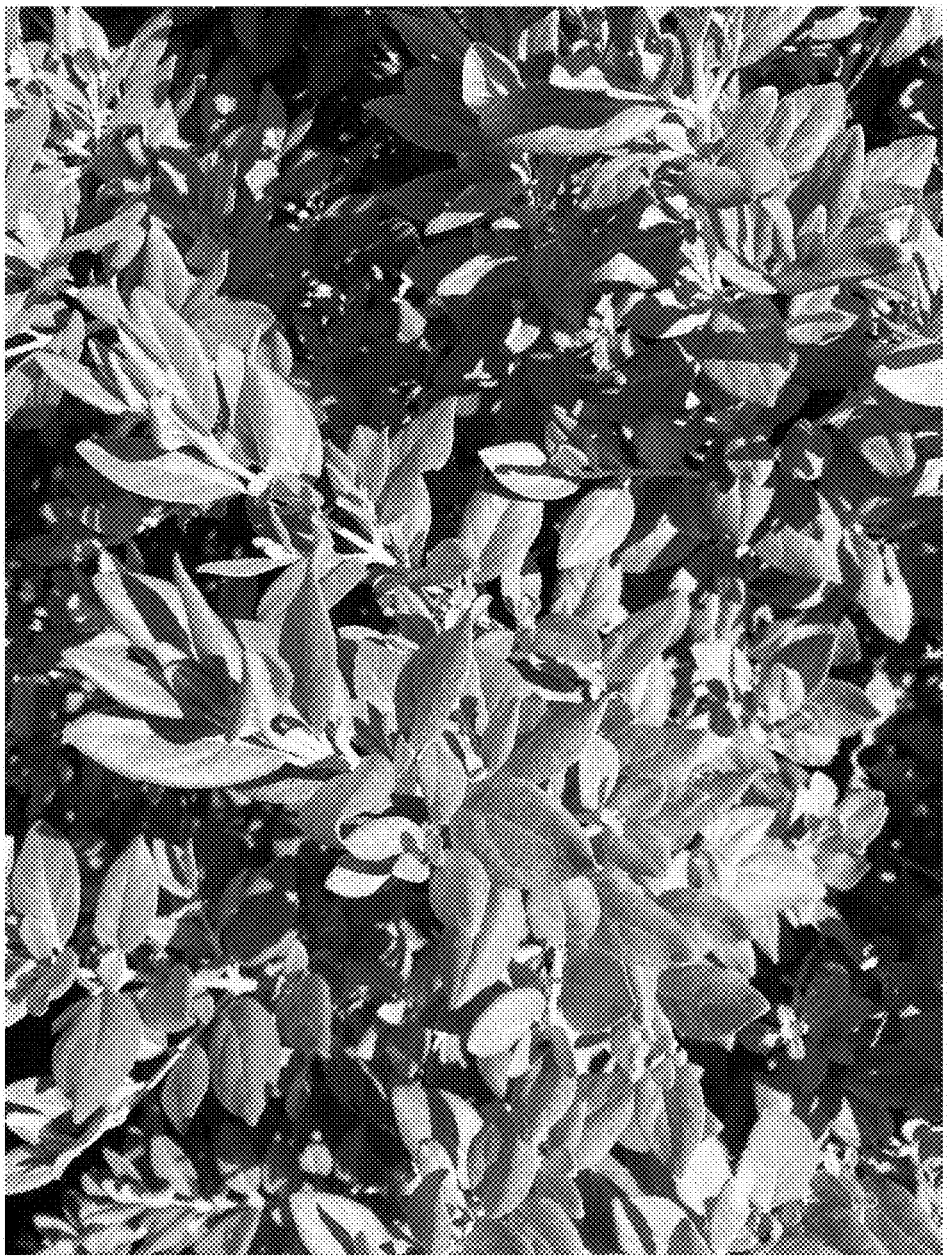

The accompanying color drawings labeled FIG. 1 and FIG. 2 illustrate the overall appearance of the new *Shepherdia* cultivar named 'Torrey' showing the colors as true as is reasonably possible to obtain in colored reproductions of this type. Colors in the photographs may differ from the color values cited in the detailed botanical description, which accurately describes the actual colors of the 'Torrey'. The photographs were made from digital photographs taken in November 2022 on plants grown outdoors in Logan, Utah.

The drawing labeled FIG. 1 depicts the entire plant.

The drawing labeled FIG. 2 depicts a close-up view of the leaves of 'Torrey'.

DESCRIPTION OF THE NEW VARIETY

The following detailed descriptions set forth the distinctive characteristics of 'Torrey'. The data which define these characteristics were collected in November 2022 in a 12 year old plant grown outdoors from asexual reproductions carried out in Logan, Utah. Color references are to The R.H.S. Colour Chart of The Royal Horticultural Society of London (R.H.S.), 5th edition (2007).

Classification:

*Family*.—Elaeagnaceae.

*Botanical*.—*Sheperdia argentea* x *Sheperdia rotundifolia*.

*Common name*.—Utah Buffaloberry.

*Variety name*.—Torrey.

Parentage:

*Female parent*.—Unnamed *Shepherdia argentea* plant.

*Male parent*.—Unnamed *Shepherdia rotundifolia* plant.

General description:

*Plant habit*.—Rounded.

*Height and spread*.—2.1×2.1 meters.

*USDA hardiness zone*.—5.

*Diseases and pests*.—Rabbits, Deer.

*Root description*.—Description: Fibrous. Color: RHS 161B.

*Propagation*.—Softwood under intermittent mist.

*Growth rate*.—30 cm to 45 cm per year.

Branches description:

*Young stems*.—Color: RHS 192D.

*Older bark*.—Color: RHS 192D.

*Branch texture*.—Pubescent.

*Average branch length*.—16.0 cm.

Foliage description:

*Leaf shape*.—Elliptical.

*Leaf base*.—Rounded.

*Leaf apex*.—Obtuse.

*Leaf margin*.—Entire.

*Leaf venation*.—Type: Pinnate. Color: RHS 192D.

*Leaf arrangement*.—Opposite.

*Leaf aspect*.—Simple.

*Leaf attachment*.—Normal.

*Leaf surface*.—Glaucous.

*Leaf size*.—Length: 3.6 cm. Width: 2.2 cm.

*Leaf color*.—Newly expanded leaves: Upper surface: RHS 190D. Lower surface: RHS 192D. Mature leaves: Upper surface: RHS 190D. Lower surface: RHS 192D.

*Leaf pubescence*.—Present.

*Leaf pubescence color*.—RHS 192D.

*Fall foliage color*.—RHS 198A (Greyish Yellow Green).

Petioles:

*Length*.—10.5 mm.

*Width*.—1 mm.

*Color*.—RHS 192D.

*Anthocyanin*.—Not present.

*Texture*.—Pubescent.

Inflorescence: Not observed.

Flower buds: Not observed.

Calyx: Not observed.

Sepals: Not observed.

Petals: Not observed.

Pedicels: Not observed.

Reproductive organs: Not observed.

Fertility: Not observed.

COMPARISON WITH PARENTAL LINES

'Torrey' is distinguished from its parents as described in Table 1:

TABLE 1

Comparison with Parental Lines

| | Female parent | 'Torrey' | Male parent |
|---|---|---|---|
| Petiole length (mm) | 5.3 ± 0.0 | 10.5 ± 1.2 | 7.0 ± 0.0 |
| Leaf length (mm) | 24.0 ± 0.7 | 39.3 ± 3.3 | 42.5 ± 0.5 |
| Leaf width (mm) | 23.3 ± 0.3 | 24.5 ± 1.2 | 12.7 ± 0.3 |
| Leaf length/width | 1.0 ± 0.0 | 1.6 ± 0.1 | 3.4 ± 0.1 |

COMPARISON WITH CLOSEST COMMERCIAL VARIETY

'Torrey' is distinguished from commercial variety *Sheperdia argentea* 'Totem' (unpatented) as described in Table 2:

TABLE 2

Comparison with Commercial Variety

| | 'Torrey' | 'Totem' |
|---|---|---|
| Plant width | Wider than 'Totem' | Narrower than 'Torrey' |
| Plant height | Shorter than 'Totem' | Taller than 'Torrey' |
| Produces flowers | No | Yes (yellow flowers) |

We claim:

1. A new and distinct variety of *Shepherdia* plant named 'Torrey' as shown and described herein.

* * * * *